United States Patent [19]

Agrawala et al.

[11] Patent Number: 5,002,774
[45] Date of Patent: Mar. 26, 1991

[54] SUSTAINED RELEASE PHARMACEUTICAL TABLET

[75] Inventors: Prafulla Agrawala, Columbus; Nageswara R. Palepu, Dublin; Brian K. Boyd, Columbus, all of Ohio

[73] Assignee: Erbamont, Inc., Minnesota, Minn.

[21] Appl. No.: 363,038

[22] Filed: Jun. 8, 1989

[51] Int. Cl.$^5$ .................................................. A61K 9/20
[52] U.S. Cl. ..................................... 424/468; 424/465; 424/469; 424/470; 424/488
[58] Field of Search ............... 424/470, 473, 469, 468, 424/488, 465

[56] References Cited

U.S. PATENT DOCUMENTS

| | | | |
|---|---|---|---|
| 3,456,049 | 7/1969 | Hotko et al. | 424/22 |
| 4,415,555 | 11/1983 | Anabuki et al. | 424/147 |
| 4,670,248 | 6/1987 | Schricker et al. | 424/438 |
| 4,708,874 | 11/1987 | DeHaan et al. | 424/470 |
| 4,756,911 | 7/1988 | Drost et al. | 424/470 |
| 4,844,907 | 7/1989 | Elger et al. | 424/470 |

OTHER PUBLICATIONS

Standard Process Labs product label for Magnesium Lactate Capsules, 1988.
G. D. Searle advertisement for Slow-Mag ®, 1988.

Primary Examiner—Thurman K. Page
Attorney, Agent, or Firm—Thompson, Hine and Flory

[57] ABSTRACT

A sustained release solid composition for delivering an amount of a pharmaceutical material, prticularly magnesium lactate, to the gastro-intestinal tract comprising:
  an active pharmaceutical powder material;
  a compressibility aid material for improving the compressibility of said pharmaceutical powder material;
  a first solid water soluble and/or swellable hydrophilic polymer; and
  microcrystalline cellulose to enable said active pharmaceutical material to be gradually released in the gastro-intestinal tract over a period of time;
  said solid composition being compressed in tablet form, and a method for producing the tablets is disclosed.

26 Claims, No Drawings

SUSTAINED RELEASE PHARMACEUTICAL TABLET

BACKGROUND OF THE INVENTION

1. Field of the Invention

The present invention relates to a novel sustained release pharmaceutical tablet, and more particularly, a sustained release magnesium lactate pharmaceutical tablet.

2. Description of Prior Art

Within the past few years, increased attention has been placed on the maintenance of a sufficient amount of magnesium in the human body. The maintenance of proper amounts of magnesium can help prevent myocardial ischemia and infarction, electrolyte deficiency resulting from malnutrition or diuretics and complications of treatment with digitalis glycosides and type 1 or 3 antiarrhythmic drugs. *Cardiovascular News*, Oct. 1986, Vol. 50, No. 10, Page 5.

Recent studies have suggested that supplementing the diet with magnesium may be effective in reducing the likelihood of arrhythmia *Cardiovascular News*, Oct. 1986, Vol. 50, No. 10, Page 5; *Modern Medicine*, July 1986, Vol. 54, No. 7, Pages 136–138; *Modern Medicine*, April 1983, Vol. 51, No. 4, Page 153; *The Lancet*, Vol. 2, No. 8566, Oct. 31, 1987, Page 1019; *Circulation*, Vol. 77, No. 2, Pages 392–397, February 1985; and *Medical World News*, Vol. 27, No. 7, Apr. 14, 1986, Pages 40–41.

Means for providing magnesium to the human body as a supplement have been proposed in the art For example, for the treatment of arrhythmia, magnesium sulfate has been intravenously administered to patients. Other dietary supplements have included magnesium oxide, magnesium hydroxide and magnesium carbonate. Despite the ability of these compounds to increase magnesium levels, they are primarily insoluble in the gastro-intestinal tract, and hence, not easily delivered to the gastro-intestinal system.

G. D. Searle and Co. has commercially marketed the "Slow-Mag" magnesium chloride delayed release composition as a magnesium supplement. The active magnesium chloride material is highly soluble, and is capable of being released over a gradual period of time. In practice, the magnesium chloride tablet is coated with an enteric coating to enable the magnesium chloride to be released and absorbed in the small intestine, and not in the stomach.

Standard Process Labs, Inc., of Palmyra, Wisconsin has sold gelatin capsules containing magnesium lactate powder. Each capsule contains approximately 70 milligrams of magnesium lactate. The amount of magnesium maintained within the capsules is relatively small, totaling to less than one milliequivalent. Accordingly, to administer a large dose of magnesium for therapeutic treatment, for example 7 milliequivalents, approximately 12 capsules have to be consumed on a daily basis. Needless to say, the high quantity of capsules which have to be swallowed per day can be burdensome. Moreover, once the capsule walls have been dissolved by the gastro-intestinal system, the entire contents of the capsule are immediately distributed to the gastro-intestinal system, and are not gradually released over a period of time. If too much magnesium lactate is delivered to one portion of the gastro-intestinal tract at one time, side effects, for example diarrhea, lesions and chemical imbalance may result.

Because of the high solubility of magnesium lactate in the gastro-intestinal system, it would be particularly desirable to develop a product which is capable of gradually releasing magnesium lactate to the gastro-intestinal system over an extended period of time, for example 7 to 12 hours. The ideal form for such a composition is a gradual-release tablet. Gradual-release tablets are known in the art. Examples of such tablets are set forth in U.S. Pat. No. 3,456,049, assigned to Ciba Corporation. To date, magnesium lactate has not been manufactured in tablet form. It is hypothesized that magnesium lactate has not been produced in tablet form because it is a highly non-compressible powder material. As such, it is extremely difficult to compress the material into tablet form.

Accordingly, there exists a need in the art for a gradual release pharmaceutical composition, and particularly a gradual release magnesium lactate tablet which supplies magnesium to the gastro-intestinal tract over an extended period of time with reduced risk of side effects.

SUMMARY OF THE INVENTION

In accordance with the present invention, a solid composition capable of delivering an amount of a pharmaceutical powder material to the gastro-intestinal tract over a period of time is provided. The delivery of the pharmaceutical composition is sustained in the sense that it gradually releases the active material to continually provide a source of the active material and minimize the occurrence of side effects. The composition is small enough in size to be maintained in tablet form and is ingested into the human gastro-intestinal tract by swallowing. In particular, the composition of the present invention is designed to deliver magnesium lactate to the gastro-intestinal tract over a 7 to 12 hour period.

Accordingly, one embodiment of the present invention provides a sustained release solid composition for delivering an amount of a pharmaceutical material to the gastro-intestinal tract comprising:

an active pharmaceutical powder material;

a compressibility aid material for improving the compressibility of said pharmaceutical powder material;

a first solid water soluble and/or swellable hydrophilic polymer; and microcrystalline cellulose to enable said active pharmaceutical material to be gradually released in the gastro-intestinal tract over a period of time;

said solid composition being compressed in tablet form.

In the preferred embodiment, the active pharmaceutical powder material comprises magnesium lactate, the compressibility aid material comprises a mixture of carnauba wax, stearic acid and solid polyethylene glycol present in an amount ranging from about 5 parts to about 15 parts per 100 parts of the composition. The first solid water soluble and/or swellable hydrophilic polymer is preferably solid polyethylene glycol and is present in an amount ranging from about 5 to 10 parts per 100 parts of composition. The amount of microcrystalline cellulose ranges from about 4 to about 9 parts per 100 parts of composition.

In another embodiment, a method for supplying magnesium over a period of time is provided. The method comprises the step of administering one or more of the above-defined sustained release magnesium lactate tablets.

In the preferred embodiment, the tablets contain approximately 7 milliequivalents of magnesium lactate and the treatment comprises either swallowing one tablet every 7 to 10 hours or swallowing two tablets twice daily.

Another embodiment of the present invention provides a method for producing a sustained release pharmaceutical composition for consumption in tablet form. The method comprises the steps of:

adding an amount of a compressibility aid material to an active pharmaceutical powder material to form a first mixture;

adding an amount of a solid water soluble and/or swellable hydrophilic polymer and an amount of microcrystalline cellulose to said first mixture to form a second mixture; and compressing said mixture into a tablet.

Accordingly, it is an object of the present invention to provide a sustained release solid composition for delivering an amount of a pharmaceutical material, and in particular magnesium lactate, to the gastro-intestinal tract with minimal side effects.

Another object of the present invention is to provide a method for supplying magnesium over a period of time.

A further object of the present invention is to provide a method for producing a sustained release pharmaceutical composition for consumption in tablet form.

These, and other objects will be readily apparent to one skilled in the art as reference is made to the following detailed description of the preferred embodiment.

DETAILED DESCRIPTION OF THE PREFERRED EMBODIMENT

While referring to the preferred embodiment, certain terminology will be utilized for the sake of clarity. The terminology is intended to encompass the recited embodiment, as well as all technical equivalents which perform substantially the same function, in substantially the same way, to achieve substantially the same result.

The present invention provides a sustained release solid composition in tablet form for delivering an amount of a pharmaceutical material to the gastro-intestinal tract. The tablet includes an active pharmaceutical powder material, a compressibility aid material for improving the compressibility of the pharmaceutical powder material, a first solid water soluble and/or swellable hydrophilic polymer and microcrystalline cellulose.

The active pharmaceutical powder material preferably is magnesium lactate (2-hydroxypropanoic acid magnesium salt). Magnesium lactate provides a source of magnesium to the human body as a nutritional supplement. Magnesium lactate is a highly non-compressible white powder crystalline substance. In the preferred embodiment, the amount of magnesium lactate in the tablet ranges up to about 76 parts per 100 parts of composition and the magnesium lactate grains have a particle size ranging between about 10 and about 250 microns.

Although the preferred embodiment provides for magnesium lactate as the active pharmaceutical powder material, the inventors hypothesize that other pharmaceutically active solid materials may be utilized. An example of one such material is nicotinic acid (3-pyridinecarboxylic acid).

The tablets of the present invention also include a compressibility aid material for improving the compressibility of the magnesium lactate powder. It is believed that in practice the compressibility aid encases the grains of the magnesium lactate powder. The encasing material, in comparison to the magnesium lactate powder, is highly compressible and as such, may be easily compressed into tablet form. The compressibility aid includes both an amount of a water insoluble waxy material and an amount of a water soluble and/or swellable polymeric material.

Pharmaceutically acceptable waxes are known in the art as compressibility aids. The waxes function to help bind the magnesium lactate powder, prevent rapid disintegration and promote sustained release of magnesium lactate. Waxes are thermo-responsive water insoluble materials which melt at higher than room temperature, can facilitate mixing with magnesium lactate and other ingredients, and can congeal at room temperature to help produce a solid mass which can be compressed. Examples of waxes which may be selected include beeswax, white wax, emulsifying wax, hydrogenated vegetable oil, cetyl alcohol, stearyl alcohol, free wax acids such as stearic acid; esters of wax acids; propylene glycol monostearate and glyceryl monostearate; and carnauba wax. In practice, a combination of carnauba wax and stearic acid is particularly preferred with the ratio of carnauba wax to stearic acid ranging from about 0.7-1.3 parts carnauba wax per 1 part stearic acid.

The compressibility aid also includes a water soluble and/or swellable polymeric material. The purpose of the water soluble and/or swellable polymeric material, in addition to aiding in compressibility, is to enable release of the magnesium lactate once it is in the gastro-intestinal tract. If no water soluble and/or swellable polymer were present in the compressibility aid material, the water insoluble waxy material could completely encase the individual magnesium lactate grains. The encasing layer would provide a barrier against release of the magnesium lactate as the encasing layer would be water insoluble. By maintaining an amount of a water soluble and/or swellable polymer, once the tablet is in the gastro-intestinal tract, the water soluble and/or swellable polymer dissolves or swells to enable the magnesium lactate to be released.

In practice, the water soluble and/or swellable polymer present in the compressibility aid material is solid polyethylene glycol, having a molecular weight greater than 400. Solid polyethylene glycol having a molecular weight of 8000 is particularly preferred.

The ratio of water soluble and/or swellable polymer to water insoluble waxy material in the compressibility aid material is from about 0.5 to 4.0 parts water soluble polymer to 10 parts water insoluble waxy material. In an embodiment where the compressibility aid includes stearic acid, carnauba wax and polyethylene glycol, a ratio of 1.4:1.6:1 has shown excellent results.

The amount of the compressibility aid material ranges from about 5 to about 15 parts to 100 parts of tablet composition. A composition containing between 8 and 11 percent compressibility aid material is particularly preferred.

The tablet composition also includes a solid water soluble and/or swellable hydrophilic polymer. The polymer is hydrophilic in that once the tablet is in the gastrointestinal tract, the gastro-intestinal fluid dissolves or swells the polymer, creating pores or openings in the tablet. Once the openings are created in the tablet, the active magnesium lactate powder can be released through the pores and into the gastro-intestinal tract. In addition to functioning as a dissolution aid, the water soluble and/or swellable hydrophilic polymer also aids in compressiblity, and in providing added mechanical strength to the composition.

Examples of water soluble and/or swellable hydrophilic polymers include solid polyethylene glycol (MW >400), hydroxymethyl cellulose, hydroxypropyl cellulose, hydroxyethyl cellulose, carboxymethyl cellulose, carboxyethyl cellulose, sodium carboxymethyl cellulose, sodium alginate, methyl cellulose, hydroxypropyl methyl cellulose, carboxypolymethylene, acacia gum, guar gum, tragencanth gum and xanthan gum. A particularly preferred polymer is polyethylene glycol having a molecular weight of 8000.

The amount of the water soluble and/or swellable polymer ranges from about 5 to about 10 parts per 100 parts of tablet composition. A tablet containing 7 to 9 percent polyethylene glycol produces particularly beneficial results.

The tablet composition also includes microcrystalline cellulose. Microcrystalline cellulose, sold under the trade name Avicel, is a non-fibrous cellulose powder commonly used in pharmaceutical tablet compositions as a binder-disintegrant. As used in the present invention, the microcrystalline cellulose acts to enable the magnesium lactate to be gradually released in the gastro-intestinal tract over a period of time. It is hypothesized that the microcrystalline cellulose provides a wicking phenomenon in that it draws gastro-intestinal fluid into the tablet matrix to initiate the dissolution process wherein the active magnesium lactate is released through the pores created in the water soluble and/or swellable hydrophilic polymer.

The tablet composition includes about 4 to about 9 parts microcrystalline cellulose per 100 parts composition. An amount between 7 and 8 percent microcrystalline cellulose is particularly preferred. It is believed that the water soluble and/or swellable polymer and microcrystalline cellulose form a matrix which houses the encased magnesium lactate particles.

The tablets of the present invention may include other additives commonly used in pharmaceutical tablets. Examples of such additives include colorants such as Opadry YS-1-2456, a light orange film-coating blend which gives tablets a peach color, FD&C Yellow #6 as Aluminum Lake, which internally colors the tablets yellow; and lubricants/glidants such as calcium stearate, magnesium stearate, fumed silicon dioxide (Cab-O-Sil), talc, glyceryl behenate (Compritol 888) and hydrogenated vegetable oil (Sterotex K). The above additives typically comprise less than 5 percent of the tablet composition, and typically less than 1 per cent of the composition.

To produce the magnesium lactate tablets, the following method is utilized. Magnesium lactate powder is sized to appropriate particle size, typically by passing through a screen and is introduced into a mixer, for example a planetary or a lodige mixer. The mixer is heated to about 50°-80° C. The compressibility aid material, for example stearic acid, carnauba wax and polyethylene glycol (MW=8000) is heated to cause the compressibility aid material to melt. The heated compressibility aid material is then added to the mixer and the resulting mixture is mixed thoroughly so that the aid material encases the grains of magnesium lactate.

The mixture is then removed from the mixer and cooled to room temperature, for example by spreading the mixture on trays. Once cooled, the mixture is optionally sized, for example, by passing through a mill, such as a Fitz Mill having a screen. The mixture is introduced into a mixing device such as a Double-cone or V-blender, and the water soluble and/or swellable polymer, for example polyethylene glycol (MW=8000), and microcrystalline cellulose is introduced into mixing device and the device is activated to thoroughly mix the components and cause the encased grains to be maintained in a matrix formed by the water soluble and/or swellable polymer and the microcrystalline cellulose.

After the components have been mixed, a tabletting lubricant, for example, calcium stearate is introduced and mixed into the mixture and the resulting mixture is removed from the blender. The resulting mixture is inserted into a tabletting press such as a Stokes B-2 tablet press, and the mixture is compressed to form a tablet. In practice, the shape of the tablet is determined by the tooling of the press. A tablet in the shape of a caplet is particularly preferred.

The above method is capable of producing tablets which weigh between 470 and 1570 mgs and contain between 3 and 10 milliequivalents of magnesium present as magnesium lactate. In comparison to prior art capsules which contain magnesium lactate grains, the tablets of the present invention contain from about 7 to about 15 more times the amount of active magnesium.

In a particularly preferred embodiment, the tablets contain about 7 milliequivalents of magnesium and are capable of releasing greater than 8 to 15 times the amount of magnesium lactate into the gastro-intestinal tract than prior art magnesium lactate pharmaceuticals. Further, the sustained release properties deliver the magnesium lactate over an extended period of time, typically ranging from about 7 to 14 hours, thus reducing the likelihood of undesirable side effects such as diarrhea. To provide a supplement of about 20 to 30 milliequivalents of magnesium to the human gastrointestinal tract, it is recommended that the patient swallow two tablets twice daily, or one tablet three times a day.

The invention is further illustrated by the following non-limiting examples.

Example 1

76 parts of magnesium lactate powder (dihydrate) is passed through a 0.0469 inch screen and introduced into a lodige mixer. The mixer is heated to 50° to 80° C. 3.2 parts of stearic acid, 3.6 parts of carnauba wax and 2.3 parts of polyethylene glycol (MW=8000) are heated to 90° to 100° C. and are introduced into the mixer. The mixer is activated for 3 minutes to ensure uniform mixing. The resulting mixture is then spread onto trays and cooled to room temperature. Once cooled, the mixture is passed through a Fitz Mill having a 0.109 inch screen and introduced into a V-blender. 7.2 parts of microcrystalline cellulose and 7.2 parts of polyethylene glycol (MW=8000) are introduced into the blender and the blender is activated for 10 minutes to provide a uniform mixture. 0.5 parts of calcium stearate, a tabletting lubricant, is added to the blender.

The mixture is removed from the blender and is compressed into tablets in a Stokes B-2 tabletting press having caplet shaped tooling (0.745"×0.306").

The materials were added in the above proportions to produce tablets having an overall weight of 1100 mg (834.6 mg magnesium lactate). The tablets produced contained about 7 milliequivalents of magnesium.

The tablets were tested for friability and capping in accordance with standardized USP test procedures. The tablets had low friability, and showed no capping.

Dissolution of the tablet was performed by placing the tablet in simulated gastric fluid (without enzymes) for two hours and then in simulated intenstinal fluid (without enzymes) for 5 hours. The tablet released 82% of the magnesium lactate into solution over a period of 7 hours. The dissolution profile for the tablet is set forth in Table 1.

Comparative Example 2

The experiment of Example 1 was repeated with the exception that 4 parts of microcrystalline cellulose and 2 parts of polyethylene glycol were added to the blender instead of 7.2 parts of each. The dissolution profile is shown in Table 1. While the dissolution performance was satisfactory, the friability performance of the tablets was poor.

Comparative Example 3

The experiment of Example 1 was repeated with the exception that 7.2 parts of lactose were substituted for 7.2 parts of microcrystalline cellulose. The dissolution profile is set forth in Table 1. The dissolution profile is unacceptable in that only 61% of the magnesium was released. This example demonstrates the importance of maintaining microcrystalline cellulose in the tablet.

Comparative Example 4

The experiment of Example 1 was repeated with the exception that 7.2 parts of dicalcium phosphate were substituted for 7.2 parts of microcrystalline cellulose. The dissolution profile is set forth in Table 1. As is the case with Comparative Example 3, the dissolution performance is unacceptable.

Comparative Example 5

The experiment of Example 1 is repeated with the exception that an additional 7.2 parts of microcrystalline cellulose is substituted for 7.2 parts of polyethylene glycol. The dissolution profile is shown in Table 1. The dissolution performance is unacceptable in that too much magnesium is released in a short period of time. This example demonstrates the importance of maintaining a water soluble and/or swellable polymer in the tablet composition.

Comparative Example 6

The experiment of Example 1 is repeated with the exception that 14.3 parts of lactose are introduced into the blender instead of 7.2 parts of microcrystalline cellulose and 7.2 parts of polyethylene glycol. The dissolution profile is shown in Table 1.

Comparative Example 7

The experiment of Example 1 is repeated with the exception that 14.3 parts of dicalcium phosphate are introduced into the blender instead of 7.2 parts of microcrystalline cellulose and 7.2 parts of polyethylene glycol. The dissolution profile is shown in Table 1.

TABLE 1

| TIME | Percent of $Mg^{++}$ Released | | | | | | |
|---|---|---|---|---|---|---|---|
| | Ex. 1 | Comp. Ex. 2 | Comp. Ex. 3 | Comp. Ex. 4 | Comp. Ex. 5 | Comp. Ex. 6 | Comp. Ex. 7 |
| 1 hour | 33 | 31 | 34 | 34 | 55 | 29 | 32 |
| 2 hours | 55 | 49 | 45 | 46 | 72 | 40 | 43 |
| 3 hours | 71 | 59 | 51 | 52 | 82 | 47 | 51 |
| 5 hours | 81 | 68 | 57 | 60 | 88 | 56 | 58 |
| 7 hours | 82 | 78 | 61 | 65 | 90 | 64 | 63 |

Comparative Example 8

A tablet was formed having satisfactory dissolution performance by combining 50 parts magnesium lactate, 20 parts hydroxyethyl cellulose (Natrosol 250HHX sold by Aqualon, DE), 28 parts microcrystalline cellulose, 1 part talc and 1 part magnesium stearate. To produce a tablet containing 7 milliequivalents of magnesium lactate, the weight of the tablet was 1.7 grams. This is commercially unacceptable as the tablet is impossible to swallow because of its size.

Comparative Example 9

The experiment of Comparative Example 8 was repeated except that the amount of Natrosol was reduced to 8 parts and the amount of microcrystalline cellulose was increased to 40 parts. To produce a tablet containing 7 milliequivalents of magnesium lactate, the weight of the tablet was 1.7 grams. This is commercially unacceptable as the tablet was impossible to swallow because of its size.

Having described the invention in detail and by reference to the preferred embodiments thereof, it will be apparent that modifications and variants are possible without departing from the scope of the appended claims.

What is claimed is:

1. A sustained release solid composition for delivering an amount of magnesium to the gastro-intestinal tract comprising:
   magnesium lactate powder;
   a first solid water soluble and/or swellable hydrophilic polymer;
   a compressibility aid material for improving the compressibility of said magnesium lactate powder, said compressibility aid material comprising a mixture of a water insoluble wax material and a second solid water soluble and/or swellable hydrophilic polymer in a ratio of about 0.5 to 4 parts of said second polymeric material to about 10 parts of said wax material, wherein the amount of said compressibility aid material ranges from about 5 parts to about 15 parts per 100 parts of said composition; and
   microcrystalline cellulose to enable said magnesium lactate to be gradually released in the gastro-intestinal tract over a period of time;
   said solid composition being compressed in tablet form.

2. A tablet composition for sustained release of magnesium lactate powder comprising: magnesium lactate powder; a first solid water soluble and/or swellable hydrophilic polymer; a mixture of a water insoluble wax material and a second solid water soluble and/or swellable hydrophilic polymer as a compressibility aid; and microcrystalline cellulose, said first water soluble and/or swellable polymer being present in an amount of about 5 to about 10 parts by weight per 100 parts of said composition, said microcrystalline cellulose being present in an amount of about 4 to about 9 parts by weight per 100 parts by weight of said composition, said magnesium lactate powder being present in an amount of about 3 to about 10 milliequivalents per tablet, and said mixture of said wax and said second polymer being present in an amount of about 5 to about 15 parts per 100 parts of said composition.

3. The tablet composition of claim 2 wherein said first polymer is a solid polyethylene glycol, said wax is a mixture of carnauba wax and stearic acid, and said second polymer is a solid polyethylene glycol.

4. The composition according to claim 1 wherein said water insoluble wax material is selected from the group consisting of beeswax, white wax, emulsifying wax, hydrogenated vegetable oil, cetyl alcohol, stearyl alcohol, free wax acids, esters of wax acids, propylene glycol monostearate, glyceryl monostearate and carnauba wax; and wherein said second solid water soluble and/or swellable hydrophilic polymer comprises solid polyethylene glycol.

5. The composition of claim 4 wherein said water insoluble wax material comprises a mixture of carnauba wax and stearic acid.

6. The composition according to claim 1 wherein said first solid water soluble and/or swellable hydrophilic polymer is selected from the group consisting of solid polyethylene glycol, hydroxymethyl cellulose, hydroxypropyl cellulose, hydroxyethyl cellulose, carboxymethyl cellulose, sodium carboxymethyl cellulose, sodium alginate, carboxyethyl cellulose, methyl cellulose, hydroxypropyl methyl cellulose, carboxypolymethylene, acacia gum, guar gum, tragencanth gum and xanthan gum.

7. The composition according to claim 6 wherein said first solid water soluble and/or swellable hydrophilic polymer comprises solid polyethylene glycol.

8. The composition according to claim 6 wherein the amount of said first water soluble and/or swellable polymer ranges from about 5 to about 10 parts per 100 parts of said composition.

9. The composition according to claim 8 wherein the amount of microcrystalline cellulose ranges from about 4 to about 9 parts per 100 parts of said composition.

10. The composition according to claim 9 wherein the amount of magnesium lactate powder ranges between about 3 and about 10 milliequivalents per tablet.

11. The composition according to claim 1 wherein the particle size of said magnesium lactate ranges between about 10 and about 250 microns.

12. The composition according to claim 11 wherein said compressibility aid encases grains of said magnesium lactate powder; and wherein said first water soluble and/or swellable hydrophilic polymer and said microcrystalline cellulose form a matrix for housing said encased magnesium lactate grains.

13. The tablet composition of claim 3 wherein said mixture encases grains of said magnesium lactate and said first polymer and said microcrystalline cellulose form a matrix housing said encased magnesium lactate grains.

14. A method for supplying magnesium over a period of time comprising the step of administering one or more sustained release magnesium lactate tablets including a composition comprising:
magnesium lactate powder;
a first solid water soluble and/or swellable hydrophilic polymer;

a compressibility aid material for improving the compressibility of said magnesium lactate powder, said compressibility aid material comprising a mixture of a water insoluble wax material and a second solid water soluble and/or swellable hydrophilic polymer in a ratio of about 0.5 to 4 parts of said polymeric material to about 10 parts of said wax material, and wherein the amount of said compressibility aid material ranges from about 5 parts to about 15 parts per 100 parts of said composition; and microcrystalline cellulose to enable said magnesium lactate to be gradually released in the gastro-intestinal tract over a period of time.

15. The method according to claim 14 wherein said compressibility aid comprises a mixture of stearic acid, carnauba wax and solid polyethylene glycol.

16. The method according to claim 14 wherein said first solid water soluble and/or swellable hydrophilic polymer comprises solid polyethylene glycol;
and wherein the amount of said solid polyethylene glycol is present in an amount ranging from about 5 to about 10 parts per 100 parts of said composition.

17. The method according to claim 15 wherein the amount of microcrystalline cellulose ranges from about 4 to about 9 parts per 100 parts of said composition.

18. The method according to claim 17 wherein said composition contains about 7 milliequivalents of magnesium present as a magnesium lactate.

19. The method according to claim 18 wherein said method comprises swallowing one tablet every 7 to 10 hours.

20. The method according to claim 18 wherein said method comprises swallowing two tablets twice daily.

21. A method for producing a sustained release magnesium lactate powder for consumption in tablet form comprising the steps of:
adding about 5 parts to about 15 parts per 100 parts of said composition of a compressibility aid material to magnesium lactate powder to form a first mixture, said compressibility aid material comprising a mixture of a water insoluble wax material and a solid water soluble and/or swellable polymeric material in a ratio of about 0.5 to 4 parts of said polymeric material to about 10 parts of said wax material;
adding an amount of a solid water soluble and/or swellable hydrophilic polymer and an amount of microcrystalline cellulose to said first mixture to form a second mixture; and
compressing said second mixture into a tablet 22. A sustained release solid composition for delivering an amount of nicotinic acid to the gastrointestinal tract comprising:
nicotinic acid;
a first solid water soluble and/or swellable hydrophilic polymer;
a compressibility aid material for improving the compressibility of said nicotinic acid, said compressibility aid material comprising a mixture of a water insoluble wax material and a second solid water soluble and/or swellable hydrophilic polymer in a ratio of about 0.5 to 4 parts of said polymeric material to about 10 parts of said wax material, wherein the amount of said compressibility aid material ranges from about 5 parts to about 15 parts per 100 parts of said composition; and microcrystalline cellulose to enable said nicotinic acid to be gradually released in the gastro-intestinal tract over a period of time;

said solid composition being compressed in tablet form.

23. The method according to claim 21 wherein said compressibility aid material comprises a mixture of stearic acid, carnauba wax and solid polyethylene glycol, said method comprising the additional steps of:

heating said compressibility aid material to about 90°–100° C. prior to addition to said magnesium lactate powder; and cooling said first mixture to room temperature prior to the addition of said water soluble and/or swellable hydrophilic polymer and said microcrystalline cellulose.

24. The method according to claim 23 wherein said solid water soluble and/or swellable hydrophilic polymer comprises solid polyethylene glycol; the amount of said polyethylene glycol ranges from about 5 parts to about 10 parts per 100 parts of said composition; and wherein the amount of said microcrystalline cellulose ranges from about 4 parts to about 9 parts per 100 parts of said composition.

25. The method according to claim 24 comprising the additional step of adding a lubricant to said second mixture prior to said compressing step.

26. The product produced by the method of claim 21.

* * * * *